United States Patent
Wada et al.

(10) Patent No.: US 7,035,746 B2
(45) Date of Patent: Apr. 25, 2006

(54) METHOD OF JUDGING HYDROGEN EMBRITTLEMENT CRACKING OF MATERIAL USED IN HIGH-TEMPERATURE, HIGH-PRESSURE HYDROGEN ENVIRONMENT

(75) Inventors: Yoru Wada, Muroran (JP); Tatsuo Hasegawa, Muroran (JP); Rinzo Kayano, Muroran (JP); Hirokazu Inoue, Minato-ku (JP)

(73) Assignee: The Japan Steel Works, Ltd., Tokyo (JP)

( * ) Notice: Subject to any disclaimer, the term of this patent is extended or adjusted under 35 U.S.C. 154(b) by 0 days.

(21) Appl. No.: 10/880,616

(22) Filed: Jul. 1, 2004

(65) Prior Publication Data

US 2005/0028882 A1  Feb. 10, 2005

(30) Foreign Application Priority Data

Jul. 1, 2003   (JP)   ............................ P2003-189747

(51) Int. Cl.
*G01N 37/00*   (2006.01)
*G06F 19/00*   (2006.01)

(52) U.S. Cl. .......................................... 702/82; 702/81
(58) Field of Classification Search ............ 702/34–35, 702/42, 81–82, 114, 136, 98, 99; 470/8, 470/10, 11, 17; 138/146
See application file for complete search history.

(56) References Cited

U.S. PATENT DOCUMENTS 5,700,120 A * 12/1997 Manning et al. ............. 411/389
6,213,884 B1 * 4/2001 McCarty ....................... 470/17

* cited by examiner

*Primary Examiner*—Bryan Bui
(74) *Attorney, Agent, or Firm*—Sughrue Mion, PLLC

(57) ABSTRACT

Using information about the position, orientation, and shape of a crack appeared in a judged material and information about the structure of the judged material as parameters, the stress intensity factor $K_I$ of the crack is found. Based on the stress intensity factor $K_I$, hydrogen embrittlement cracking of the judged material is judged. The crack growth rate and possibility of brittle fracture can be judged by comparing the stress intensity factor $K_I$ with the critical stress intensity factor $K_{IH}$ for crack initiation or the critical stress intensity factor $K_{IC-H}$ for brittle fracture about the temper embrittled steel which absorbs approximately 2.0 ppm hydrogen.

11 Claims, 11 Drawing Sheets

CRITICAL TRANSITION CURVE FOR HYDROGEN EMBRITTLEMENT CRACK

COMPARISON OF DATA REPRODUCING HYDROGEN ENVIRONMENT WITH CONVENTIONAL DATA

HYDROGEN EMBRITTLEMENT CRACK GROWTH CURVE OF TEMPER EMBRITTLED STEEL

FIG. 3

| VARIABLES OF ANALYSIS | SHAPE AND CRACK ANALYSIS POSITION (MARKED BY CIRCLES) |
|---|---|
| NOZZLE SCHEDULE A | NOZZLE PORTION<br>$t_n$=Spec.VALUE, $t_h=1/2 t_s$, $r_1=R_i+1/4 t_s$, $R_i$, $t_s$ |
| INNER DIAMETER $R_i$ | |
| SHELL THICKNESS $t_s$ | WELDING JOINT PORTION<br>$t_{OL}$, $t_s$ |
| OVERLAY THICKNESS $t_{OL}$ | |
| INTERNAL THICKNESS $t_a$ | INTERNAL MOUNTING PORTION<br>$t_a$, $t_s$ |
| CRACK SHAPE FACTOR a | BOTTOM HEAD PORTION<br>$t_s$, $r_1=R_i+1/4 t_s$, $t_h=1/2 t_s$ |
| CRACK SHAPE FACTOR Q | |
| DIRECTION OF CRACK | |
| PRESSURE | |

PORTIONS OF PRESSURE VESSEL THAT CAN BE ANALYZED IN TERMS OF HYDROGEN EMBRITTLEMENT CRACKING

*FIG. 5(a)* *FIG. 5(b)*
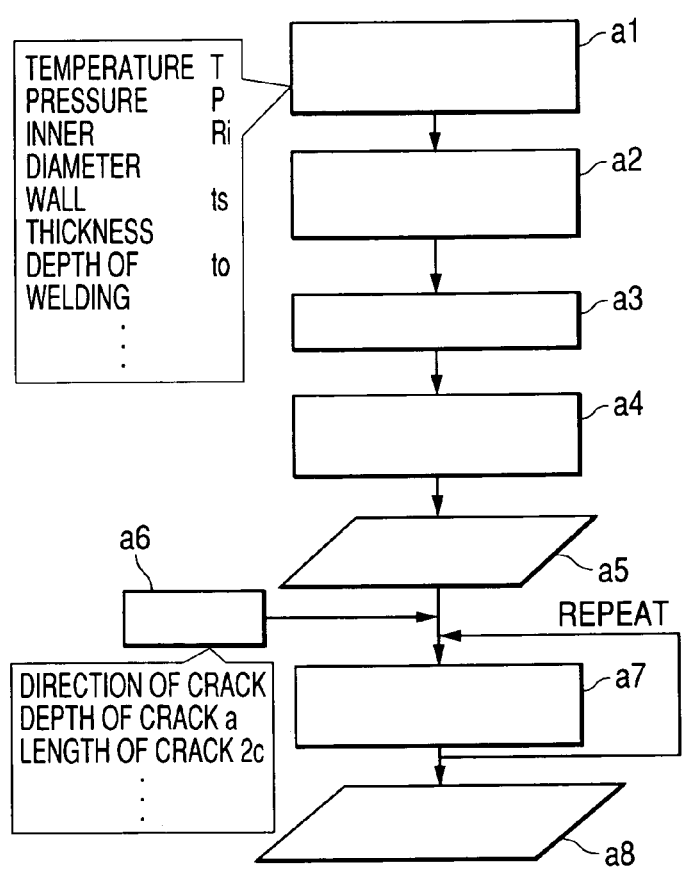
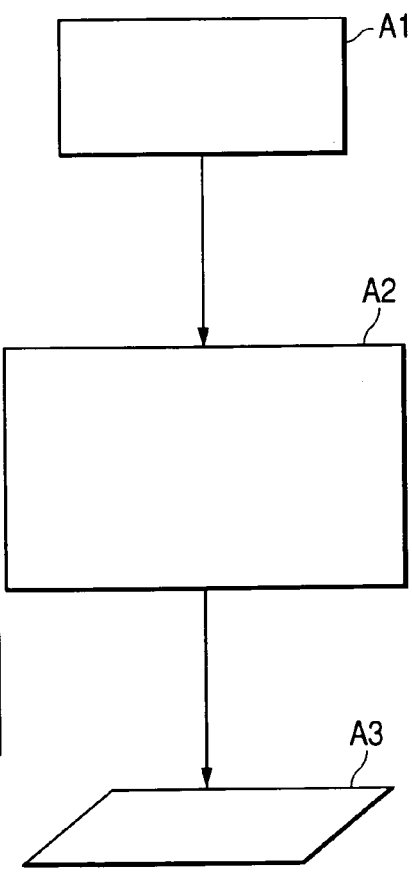

CRITICAL TRANSITION CURVE FOR HYDROGEN EMBRITTLEMENT CRACK

DEPENDENCE OF CRACK GROWTH RATE OF
HYDROGEN EMBRITTLEMENT CRACK ON
RATE OF LOADING

DEPENDENCE OF CRACK GROWTH RATE OF HYDROGEN EMBRITTLEMENT CRACK

SCHEMATIC DIAGRAM OF GROWTH RATE OF
HYDROGEN EMBRITTLEMENT CRACK EXPLAINED
IN API (AMERICAN PETROLEUM INSTITUTE)
RECOMMENDED PRACTICE 579 FIRST EDITION

METHOD OF JUDGING HYDROGEN EMBRITTLEMENT CRACKING OF MATERIAL USED IN HIGH-TEMPERATURE, HIGH-PRESSURE HYDROGEN ENVIRONMENT

The present application is based on Japanese Patent Application No. 2003-189747, the entire contents of which are incorporated herein by reference.

BACKGROUND OF THE INVENTION

1. Field of the Invention

The present invention relates to a method of judging hydrogen embrittlement cracking of a material used in a high-temperature, high-pressure hydrogen environment and, more particularly, to facility management and prediction of life of a large-sized reactor used in petroleum refining equipment.

2. Related Art (Past Method)

Since heavy walled reactors used in a petroleum refining plant are operated in a high-temperature, high-pressure hydrogen environment, there is a danger that the susceptibility of catastrophic failure is increased by hydrogen. With respect to hydrogen embrittlement cracks and damages to pressure vessels, evaluation techniques have been explained to some extent in Japan and foreign countries standards. For example, as shown in FIG. 12, a pictorial diagram of the crack growth rate due to hydrogen embrittlement appears in Non-Patent Reference 1 that is an international recommended practice giving a guide in evaluating the soundness of a pressure vessel. This diagram is a qualitative expression of crack growth in a case where a crack has occurred in a pressure vessel that has been hydrogen embrittled. The horizontal axis indicates the stress intensity factor applied to the crack tip, while the vertical axis indicates the crack growth rate. The meanings of the symbols used in the diagram are as follows.

$K_{IH}$: critical stress intensity factor for crack initiation (MPa$\sqrt{m}$)
$K_{IC-H}$: fracture toughness of hydrogen-absorbed material indicated by fast fracture (MPa$\sqrt{m}$)
$K_{IC}$: fracture toughness of hydrogen-free material (MPa$\sqrt{m}$)
da/dt: growth rate of hydrogen-assisted crack (mm/sec)

Besides, mathematical formulas for finding the stress intensity factor by simple calculations have been proposed. The mathematical formulas are shown below. The stress intensity factor is calculated by the following procedure and mathematical formulas.

1) Selection of Applied Stress ($\sigma$)
    a) Applied stress=0.2% YS
    b) Applied stress=circumferential (axial) stress+used stress+residual stress
    circumferential stress=internal pressure×(inner diameter+wall thickness)/(2×wall thickness)
    axial stress=internal pressure×(inner diameter+wall thickness)/(4×wall thickness)

2) Finding a flaw Shape Parameter (Q)

$$Q=\phi^2-0.212\times(\sigma/0.2\% \ YS)^2$$

where $\phi$ is calculation of a shape parameter using elliptical integration by the Simpson's formula 3) $K_I$ (Stress Intensity Factor)
    embedded crack: applied stress ($\sigma$)×SQR ($\pi$×crack depth (a)/flaw shape parameter (Q))
    surface crack: intrinsic crack $K_I$×1.1

Reference: API Recommended Practice 579

The evaluation method by the above-described procedures, however, has the problems that it is difficult to make quantitative evaluations, and that the evaluations is too conservative. Therefore, there is a strong demand for establishment of a flaw evaluation method that has high reliability and can make quantitative evaluations.

However, where a quantitative evaluation is made, it is difficult to estimate residual stress existed in a pressure vessel. There is the problem that a huge amount of calculations using a computer is generally necessary for analysis of heat flow and residual stress analysis.

Furthermore, the aforementioned simple calculation method can calculate stress intensity factors without needing a large-capacity computer. However, to achieve a straightforward method, residual stress is contained in the stress in work. The yield stress of the material has been adopted as the stress in work. Using the value of the yield stress of the material means that the life of the pressure vessel is evaluated too conservatively. Therefore, there is the problem that this simple calculation method does not provide high reliability of evaluation.

SUMMARY OF THE INVENTION

The present invention has been made under the above-described circumstances. It is an object of the invention to provide a predictable evaluation method for the growth of crack like flaw in the residual stress field appeared inside a pressure vessel and the danger of catastrophic failure in the pressure vessel, taking account of the effects of hydrogen embrittlement caused by high-temperature, high-pressure hydrogen gas flowing through the pressure vessel.

The present invention establishes a technique for evaluating the cracking susceptibility of a vessel, which has absorbed hydrogen. In the past, the susceptibility has been unknown. Thus, it is possible to make a decision as to whether the vessel is destroyed by hydrogen embrittlement cracking or not. Furthermore, the lowest temperature under pressurized condition can be analyzed. In addition, for calculation of a crack appeared in a weld joint of discontinuity shape, the present invention establishes an accurate, instantaneous, and straightforward method of calculation employing a technique of multivariable regression analysis. In this way, a great reduction in the analysis time has been achieved.

A method of judging hydrogen embrittlement cracking of a material used in a high-temperature, high-pressure hydrogen environment in accordance with a first embodiment of the present invention solves the foregoing problem and starts with finding a stress intensity factor $K_I$ of a crack appeared in the material to be judged, using at least information about the position, direction, and shape of the crack and information about the structure of the judged material as factors. Hydrogen embrittlement cracking of the judged material is judged according to the stress intensity factor $K_I$.

A second embodiment of the invention is based on the first embodiment and further characterized in that the factors include the depth and length of the crack, structural factors (such as nozzle diameter, inner diameter, wall thickness, and overlay thickness) of a pressure vessel that is the material to be judged, and the operating pressure.

A third embodiment of the invention is based on the first or second embodiment and further characterized in that the stress intensity factor $K_I$ is expressed by a regression formula obtained by performing a multivariable regression analysis using the factors.

A fourth embodiment of the invention is based on any one of the first through third embodiments and further characterized in that the stress intensity factor $K_I$ and critical stress intensity factor $K_{IH}$ for crack initiation are compared and a decision is made as to whether the crack like flaw has grown or not according to results of the comparison.

A fifth embodiment of the invention is based on the fourth embodiment and further characterized in that the critical stress intensity factor $K_{IH}$ for crack initiation is a quantitative expression of temperature dependence characteristics that the judged material which has been temper embrittled shows in a range of from room temperature to 150° C. in a hydrogen absorbed, temper embrittled steel.

A sixth embodiment of the invention is based on any one of the first through fifth embodiments and further characterized in that the stress intensity factor $K_I$ and critical stress intensity factor $K_{IC-H}$ for brittle fracture are compared and possibility of catastrophic failure of the pressure vessel is judged according to results of the comparison.

A seventh embodiment of the invention is based on the sixth embodiment and further characterized in that the critical stress intensity factor $K_{IC-H}$ for brittle fracture is a quantitative expression of temperature dependence characteristics that the judged material which has been temper embrittled shows in a range of from room temperature to 86° C. in a hydrogen absorbed, temper embrittled steel.

An eighth embodiment of the invention is based on any one of the first through seventh embodiments and further characterized in that the crack growth rate is judged according to a crack growth rate calculated from a rate of loading and from an operating temperature.

A ninth embodiment of the invention is based on the fifth or seventh embodiment and further characterized in that the operating temperature can be set according to which of the stress intensity factor $K_I$ and the critical stress intensity factor $K_{IH}$ for crack initiation, the factor $K_{IH}$ being dependent on temperature, or critical stress intensity factor $K_{IC-H}$ for brittle fracture is greater.

A tenth embodiment of the invention is based on any one of the first through ninth embodiments and further characterized in that the stress intensity factor $K_I$ is calculated on the condition that the pressure vessel has been shutdown.

An eleventh embodiment of the invention is based on any one of the first through tenth embodiments and further characterized in that (A) the stress intensity factor $K_I$ found on the condition that the operation has been stopped and the critical stress intensity factor $K_{IC-H}$ for brittle fracture are compared, and that (B) when a decision is not made according to the result of the comparison that there is a possibility of brittle fracture. (C) The minimum pressurizing temperature can be settled by the following procedure; (1) calculate the stress intensity factor $K_I$ at a startup condition, and (2) then evaluate the upperbound temperature where $K_I$ does not exceed $K_{IH}$ or $K_{IC-H}$ which are temperature dependent parameters.

A twelfth embodiment of the invention is based on any one of the first through eleventh embodiments and further characterized in that the judged material is a pressure vessel for petroleum refining.

That is, according to the present invention, a more reliable and quantitative evaluation of hydrogen-assisted cracking can be made by the least information of the shape of crack like flaw (including orientation) and the structure information of the pressure vessel. Consequently, an accurate evaluation can be made. Examples of the factors include the inner diameter of a pressure vessel, the internal support thickness, shell thickness, overlay thickness, operating pressure, shape of the crack (such as length, depth, and crack orientation), and the flaw shape parameter found from the shape of crack.

Where the distribution of the stress intensity factors $K_I$ is represented by a regression formula obtained by performing a multivariable regression analysis using the aforementioned factors, the hydrogen embrittlement cracking can be evaluated easily and accurately by an instantaneous and easy calculational system.

Furthermore, in the judgement of cracking due to embrittlement according to the stress intensity factor $K_I$, the results of comparison between the stress intensity factor $K_I$ and critical stress intensity factor $K_{IH}$ for crack initiation can be utilized. In particular, in a case where $K_I < K_{IH}$, it can be estimated that the crack has not grown. On the other hand, in a case where $K_I \geq K_{IH}$, it can be estimated that the crack has grown. Where growth of the crack is estimated, the crack growth rate is calculated from the rate of loading and from the operating temperature. Thus, it is possible to predict the crack growth rate, i.e., the life of the material.

In addition, in the judgement of cracking due to embrittlement according to the stress intensity factor $K_I$, the results of comparison between the stress intensity factor $K_I$ and critical stress intensity factor $K_{IC-H}$ for brittle fracture can be utilized. In particular, in a case where the stress intensity factor $K_I \geq$ the critical stress intensity factor $K_{IC-H}$ for brittle fracture, it can be judged that there is a possibility of brittle fracture. Based on the judgment, the judged material can be repaired or a replacement can be performed.

That is, the stress intensity factor $K_I$, critical stress intensity factor $K_{IH}$ for crack initiation, and critical stress intensity factor $K_{IC-H}$ for brittle fracture found as described above can show safe and desirable state of condition of a judged material. The operating temperature can be set so as to satisfy the above-described relations in magnitude by expressing the critical stress intensity factor $K_{IH}$ for crack initiation and the critical stress intensity factor $K_{IC-H}$ for brittle fracture by quantitative temperature dependence characteristics. For example, in order to achieve the safest state in which the fracture does not grow, the operating temperature may be set so as to satisfy the condition, stress intensity factor $K_I < K_{IH}$.

In the present invention, the judged material is used in a high-temperature, high-pressure hydrogen environment. Typically, a pressure vessel for heavy walled reactor employed for petroleum refining is shown. In the present invention, the type of the judged material is not restricted to certain ones. However, a typical one is 2.25Cr-1Mo steel.

BRIEF DESCRIPTION OF THE DRAWINGS

FIG. 3 shows examples of portions of a pressure vessel that can be analyzed in one embodiment of the invention, the vessel being a material to be judged;

FIGS. 5(a) and 5(b) are flowcharts illustrating a procedure for calculating a stress intensity factor in accordance with the invention (5(b)) and a related art procedure (5(a)) for calculations;

DETAILED DESCRIPTION OF THE PREFERRED EMBODIMENTS

One embodiment of the present invention is hereinafter described.

Heretofore, test data produced by high-temperature, high-pressure hydrogen charged small test specimens about 1 inch thick to evaluate hydrogen embrittlement have been published in large amounts. However, such test specimens release hydrogen in a short time and so the actual hydrogen environment in heavy walled equipment has not been reproduced. For this reason, testing about cracking due to hydrogen embrittlement has been done by equipment capable of adding hydrogen to a large-sized 3.5T-CT test specimen that is comparable in size with the actual heavy walled equipment. In this way, data collection simulating actual hydrogen environment in equipment has been made possible.

Figure 1:
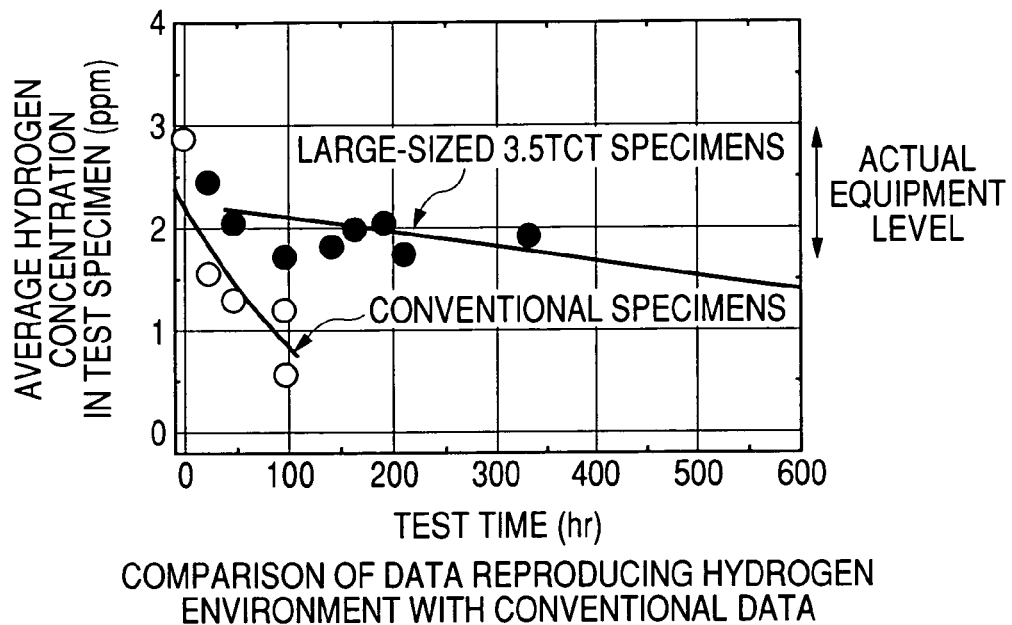
FIG. 1 shows the average hydrogen concentrations in test specimens used in one embodiment of the present invention.

In FIG. 1, the hydrogen concentrations of hydrogen charged 1T-CT test specimens of related art and high-temperature, high pressure hydrogen charged 3.5T-CT test specimens by the present equipment are plotted against test time. The inside of each 3.5T-CT test specimen is maintained at more than about. 2 ppm for such a long time enough to evaluate hydrogen-assisted cracking and in the same hydrogen concentration condition as in actual equipment. In this way, the critical characteristics of hydrogen embrittlement cracking of heavy walled reactor has been reproduced. The environment has been heretofore difficult to reproduce. Furthermore, this regeneration test can easily quantitatively show the critical stress intensity factor $K_{IH}$ for crack initiation and critical stress intensity factor $K_{IC-H}$ for brittle fracture in a hydrogen absorbed, temper embrittled state used for evaluation of hydrogen embrittlement cracking in a state where the judged material has absorbed hydrogen. Furthermore, the critical stress intensity factor $K_{IH}$ for crack initiation and critical stress intensity factor $K_{IC-H}$ for brittle fracture can be shown as quantitative expressions of the temperature dependence characteristics. These factors can be obtained by a regression analysis that reflects the degree of deterioration of the material, the amount of hydrogen, or the loading environment, for example.

Figure 2:
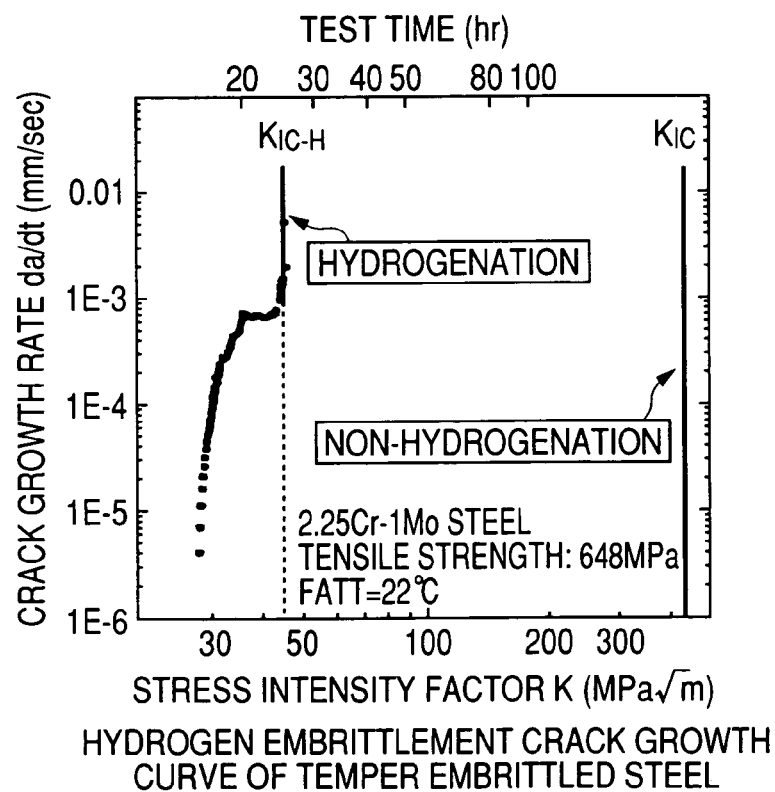
FIG. 2 shows the relation between the stress intensity factor and the crack growth rate in one embodiment of the invention.

FIG. 2 shows the relation between the crack growth rate due to hydrogen embrittlement under given test conditions and the stress intensity factor $K_I$. When hydrogen is absorbed into a temper embrittled steel, a phenomenon is observed in which growth of a crack starts when some stress intensity factor (critical stress intensity factor $K_{IH}$ for crack initiation) is exceeded and that a delayed fracture occurs after a delay of certain time. Since the stress intensity factor (critical stress intensity factor $K_{IC-H}$ for brittle fracture) when shifting to brittle fracture is made is lower than the fracture toughness $K_{IC}$ in a case where no hydrogen is charged, a decision as to whether the vessel undergoes brittle fracture can be made according to the critical stress intensity factor $K_{IC-H}$ for brittle fracture. That is, the decision can be made by finding the stress intensity factor $K_I$ of the judged material and comparing the stress intensity factor $K_I$ and the critical stress intensity factor $K_{IC-H}$ for brittle fracture. Where the stress intensity factor $K_I$ is greater than the critical stress intensity factor $K_{IC-H}$ for brittle fracture, it can be judged that the judged material has a possibility of brittle fracture. Furthermore, when the stress intensity factor $K_I$ becomes greater than the critical stress intensity factor $K_{IH}$ for crack initiation, the crack grows. Therefore, the critical stress intensity factor $K_{IH}$ for crack initiation can be used as the growth starting point of the crack for the decision.

Calculation Method of Stress Intensity Factor $K_I$

With respect to the aforementioned stress intensity factor $K_I$, a multivariable regression analysis of the crack shape, structural factors of the judged material (such as the inside radius of the vessel and wall thickness), operating pressure, and so on is performed. The stress intensity factor $K_I$ can be calculated for the crack depth a which appeared just beneath a stainless overlay, using an approximate regression formula. FIG. 3 shows portions of a pressure vessel for petroleum refining, the vessel being a judged material. These portions can be analyzed in terms of cracking due to hydrogen embrittlement. Mathematical formulas 1–7 given below are formulas indicating approximate values of the stress intensity factors of cracks appeared in an internal attachment portion shown in FIG. 3. The cracks have crack forms of a:2c=1:2 to 1:4. In the formulas, Ri is the inside radius, in inches. ta is the internal support thickness, in inches. ts is the shell thickness, in inches. P is the pressure in psi. Q is the flaw shape parameter ($Q=1+1.464\ (a/c)^{1.65}$, c=half of the crack length).

$K_I(a=0.3\ inch)=0.15332604 \cdot Ri-0.870175 \cdot ta-2.0442719 \cdot ts+0.0050014 \cdot P+85.626 \div \sqrt{Q}-2.32997$ [Mathematical Formula 1]

$K_I(a=0.5\ inch)=0.28772125 \cdot Ri-1.4318 \cdot ta-2.95045 \cdot ts+0.0100107 \cdot P+123.753 \div \sqrt{Q}-58.826$ [Mathematical Formula 2]

$K_I(a=0.7\ inch)=0.37975542 \cdot Ri-1.85075 \cdot ta-3.28693 \cdot ts+0.01226219 \cdot P+120.915 \div \sqrt{Q}-70.177$ [Mathematical Formula 3]

$K_I(a=1.0\ inch)=0.47076813 \cdot Ri-2.439125 \cdot ta-3.9638969 \cdot ts+0.0149776 \cdot P+116.77 \div \sqrt{Q}-76.03$ [Mathematical Formula 4]

$K_I(a=1.5\ inches)=0.58827708 \cdot Ri-3.09885 \cdot ta-5.1434438 \cdot ts+0.01876205 \cdot P+117.07 \div \sqrt{Q}-82.61$ [Mathematical Formula 5]

$K_I(a=2.0\ inches)=0.68942521 \cdot Ri-3.544075 \cdot ta-6.3255906 \cdot ts+0.02211337 \cdot P+123.96 \div \sqrt{Q}-90.06$ [Mathematical Formula 6]

$K_I(a=3.0\ inches)=0.87130875 \cdot Ri-3.7426 \cdot ta-8.5906813 \cdot ts+0.0282453 \cdot P+147.72 \div \sqrt{Q}-109.03$ [Mathematical Formula 7]

Where the crack shape is a crack given by a:2c=1:4 to 1:16, the stress intensity factor $K_I$ can be found by a procedure similar to the above-described procedure, using the results of multivariable regression obtained by a procedure similar to the above-described procedure.

Subsequently, with respect to portions other than the internal attachment portion (i.e., positions where generation of cracks is assumed such as nozzle, weld joint portion, and head portion as shown in FIG. 3), the stress intensity factor $K_I$ can be found accurately for the crack depth a.

Figure 4A:
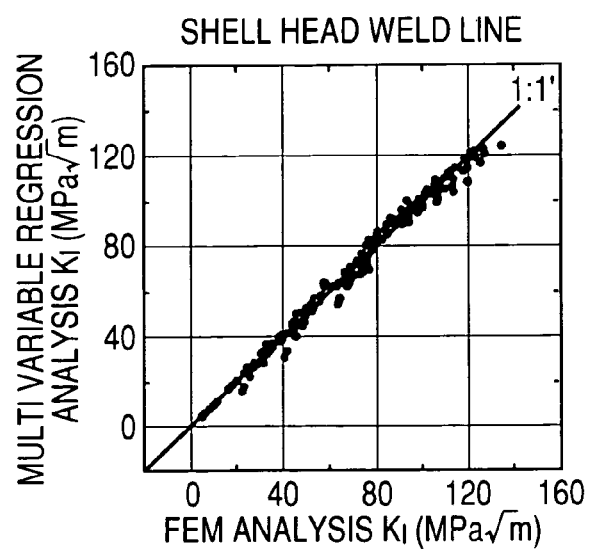
FIGS. 4(a), 4(b) and 4(c) show stress intensity factors obtained by multivariable regression analyses in accordance with one embodiment of the invention and stress intensity factors obtained by FEM analyses are compared.
Figure 4B:
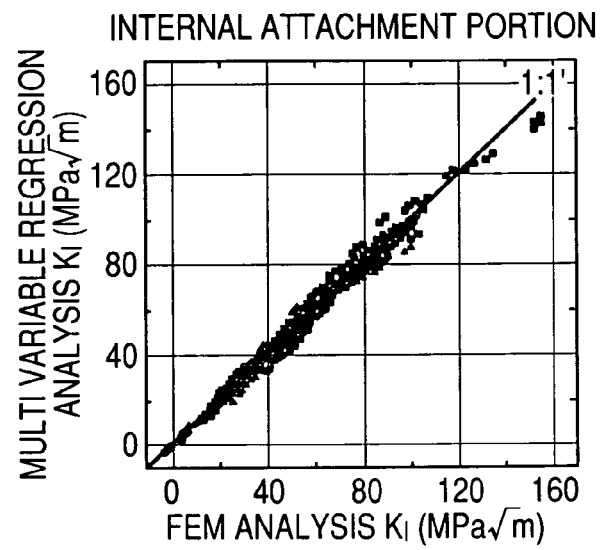
Figure 4C:
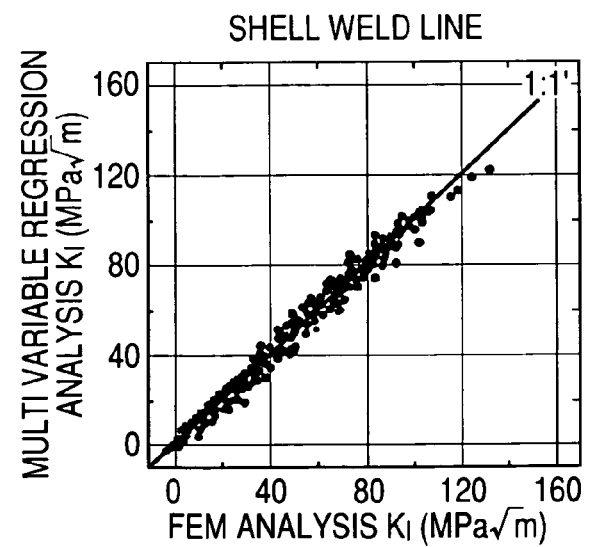

The approximation accuracy of this method of calculation is higher than 95% of a finite element method (FEM) implemented by performing a large number of finite element analyses taking account of thermal stresses and pressure generated by the difference in coefficient of thermal expansion between the base material and the inside stainless overlay as shown in FIG. 4. That is, a long processing time has been required for FEM calculations heretofore. These simple formulas make it possible to output the results of analyses of the stress intensity factor $K_I$ instantaneously.

The simplified procedure of calculations described above and the past procedure of FEM analyses are compared in FIGS. 5(a) and 5(b). As is obvious from FIGS. 5(a) and 5(b), in the past method, operating conditions and data about the structure of the vessel are entered (step a1). Then, division into meshes taking account of cracks is performed for finite elements (step a2). An FEM thermal analysis is performed (step a3). Then, an elastoplastic FEM analysis based on thermal stresses and membrane stresses is performed (step a4). The distribution of stresses in the overlay welding part is found (step a5). Furthermore, information about cracking is entered (step a6). Calculations for analysis of the stress intensity factor taking account of the distribution of stresses are performed repeatedly (step a7). As a result, the distribution of stress intensity factors near the overlay welding part is obtained (step a8).

On the other hand, in the simple procedure of calculations adopted in the present invention, data about the structure of the welding of the judged material and information about cracks are entered (step A1). Using these as factors, stress intensity factors are found by a multivariable analysis (step A2). As a result, the distribution of the stress intensity factors near the overlay welding part is obtained (step A3).

As shown in FIGS. 5(a) and 5(b), in the related art method, a huge amount of calculation using a computer has been heretofore required for thermal flow and stress analysis to calculate cracks appeared in a weld joint of discontinuity shape. Great reductions in analysis time and cost can be accomplished by constructing an accurate instantaneous, simple calculation technique using the technique of multivariable regression analysis according to the present invention as described so far.

Figure 6:
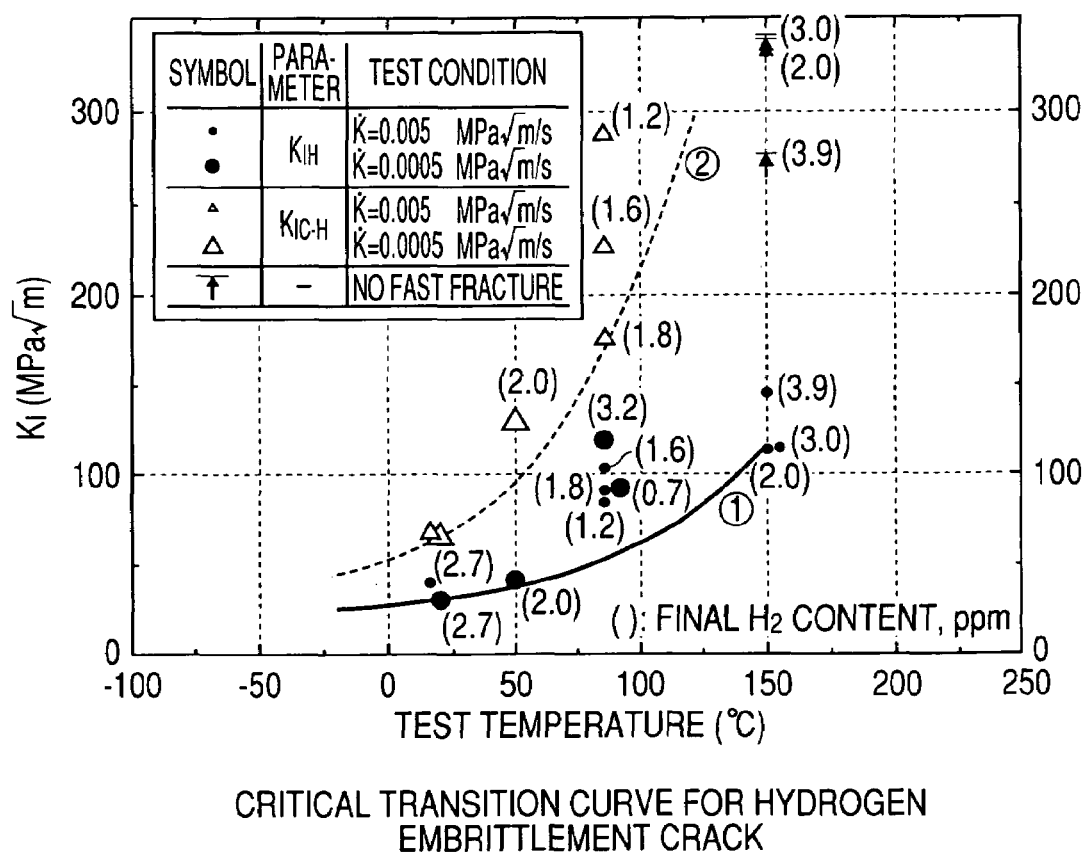
FIG. 6 shows a critical transition curve for hydrogen embrittlement cracking in one embodiment of the invention.

In FIG. 6, the relations of the factors $K_{IH}$ and $K_{IC-H}$ to the environmental temperature are shown. The factor $K_{IH}$ at 150° C. increased to a value that was about four times as large as the value obtained at room temperature, although 3.9 ppm of hydrogen was detected, at maximum, from within the test specimen. Connecting the lower limit points of these data resulted in the critical stress intensity factor $K_{IH}$ for growth of hydrogen assisted cracks in a case where temper embrittled 2.25Cr-1Mo steel absorbed hydrogen. The relation of this factor to the environmental temperature T can be given by Mathematical Formula 8.

$K_{IH}$=20+80exp[0.0164×
(T−138)](MPa√m,° C.)  [Mathematical Formula 8]

Furthermore, since the critical stress intensity factor $K_{IC-H}$ for brittle fracture was not observed at 150° C., the critical stress intensity factors for hydrogen-assisted brittle fracture of 2.25Cr-1Mo steel that was temper embrittled under a hydrogen environment simulating actual equipment can be given in a range from about 20 to 86° C. by Mathematical Formula 9.

$K_{IC-H}$=20+80exp[0.0185×
(T−50)](MPa√m,° C.)  [Mathematical Formula 9]

The temperature (T) at which the vessel can be pressurized safely can be found from Mathematical Formula 10 that is a modification of Mathematical Formula 8 to prevent the stress intensity factor $K_I$ from exceeding the critical stress intensity factor $K_{IH}$ for initiation of a hydrogen embrittlement crack.

T=138+1/0.0164 ln[($K_I$−20)/80]  [Mathematical Formula 10]

Furthermore, in judging hydrogen embrittlement, the growth rate of a hydrogen embrittlement crack da/dt that can be used for prediction of life can be used.

This growth rate can be obtained, for example, by a regression analysis in which the degree of deterioration of the material, the amount of hydrogen, or the loading environment is reflected.

Figure 7:
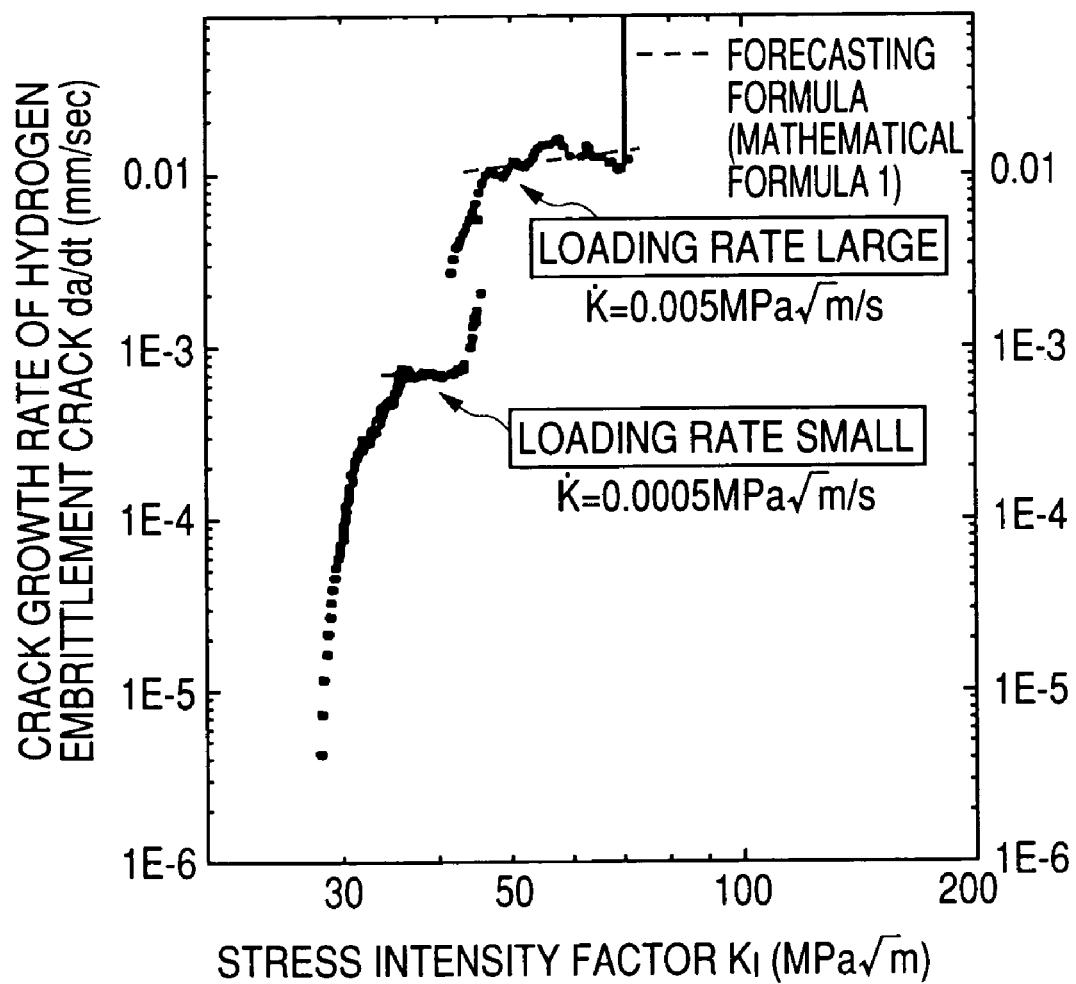
FIG. 7 shows the dependence of the relation between the growth rate of a hydrogen embrittlement crack and the stress intensity factor on the rate of loading in one embodiment of the invention.

In particular, the growth rate of a hydrogen embrittlement crack fracture da/dt shows strong dependence on variation of the rate of loading as shown in FIG. 7. The growth rate increases with increasing the rate of loading. From these data analyses and from the relation between the stress intensity factor $K_I$ and its rate of change $\dot{K}$ (K dot), the growth rate of a hydrogen embrittlement crack at room temperature can be given by the following Mathematical Formula 11.

(da/dt)$_{RT}$=0.03733×$\dot{K}$^0.067×$K$^(3.616+0.895 log $\dot{K}$)
(mm/sec,MPa√m,MPa√m/s)  [Mathematical Formula 11]

where $K_{IH}$<$K_I$<$K_{IC-H}$, $\dot{K}$=0.0005~0.005 MPa√m/sec

Figure 8:
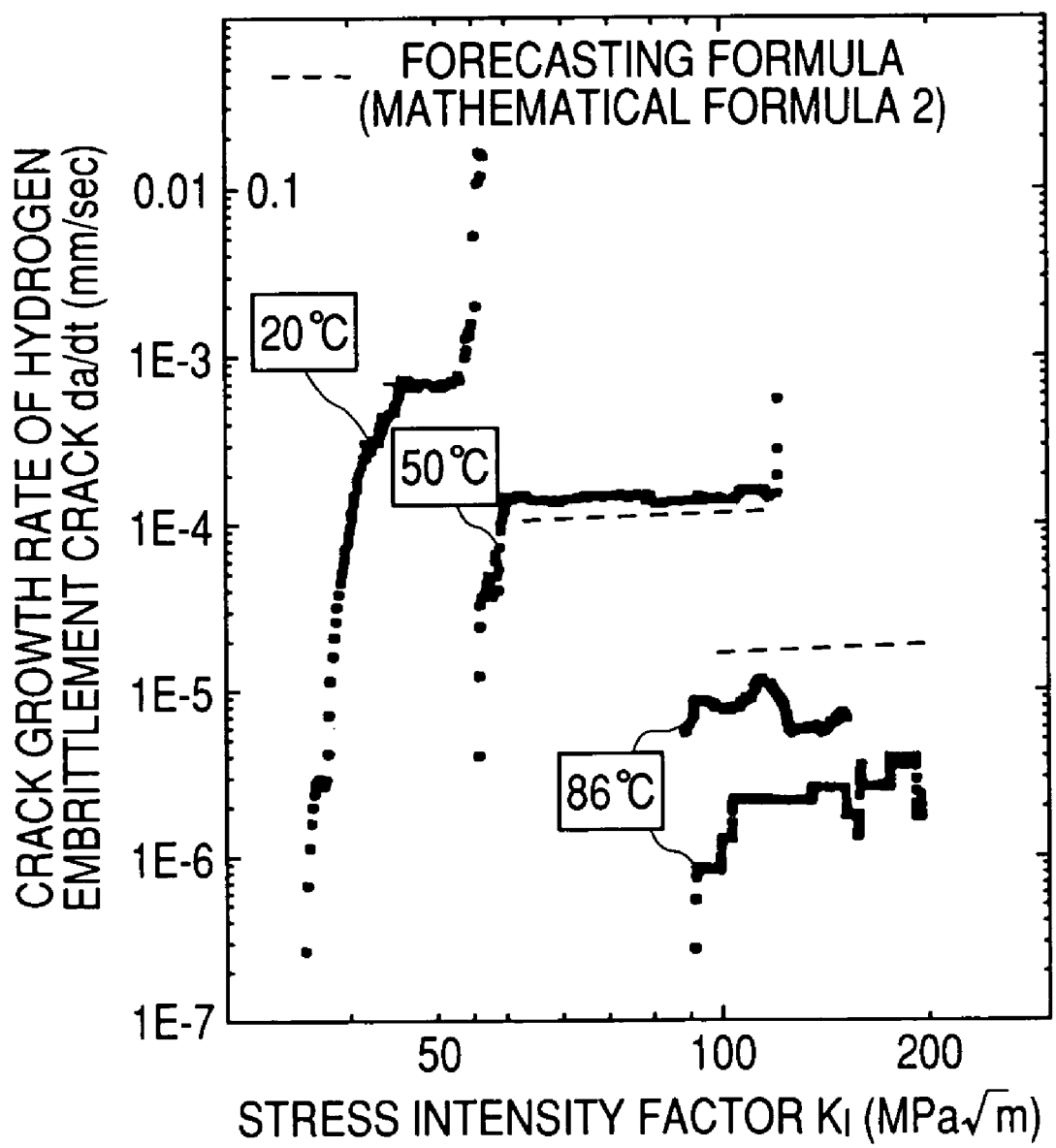
FIG. 8 shows the dependence of the relation between the growth rate of a hydrogen embrittlement crack and the stress intensity factor on the environmental temperature in one embodiment of the invention.

Furthermore, the growth rate da/dt of a hydrogen embrittlement crack decreases with increasing the environmental temperature as shown in FIG. 8. These data analyses and consideration of both the environmental temperature and the rate of loading described above make it possible to estimate the growth rate of a hydrogen embrittlement crack under the actual equipment environmental temperature and varying loading rate conditions from Mathematical Formula 12 given below. Directly expressing Mathematical Formula 12 in terms of actual equipment environmental temperature and varying loading rate gives rise to Mathematical Formula 13.

(da/dt)$_{T° C.}$=(da/dt)$_{RT}$×exp[6406×(1/(T+273)−1/293)],
(mm/sec,MPa√m,MPa√m/s),°C.)  [Mathematical Formula 12]

where $K_{IH}$<$K_I$<$K_{IC-H}$, $\dot{K}$=0.0005~0.005 MPa√m/sec, T=20 to 86° C.

[Mathematical Formula 13]

$$\frac{da}{dt} = CK^n \times \exp\left\{6206 \times \left(\frac{1}{T+273} - \frac{1}{293}\right)\right\} \times \alpha$$

where C=0.0373×$\dot{K}$^−0.6067 n=1.269+log $\dot{K}$(mm/sec,MPa√m,° C.,MPa√m/s)

Figure 9:
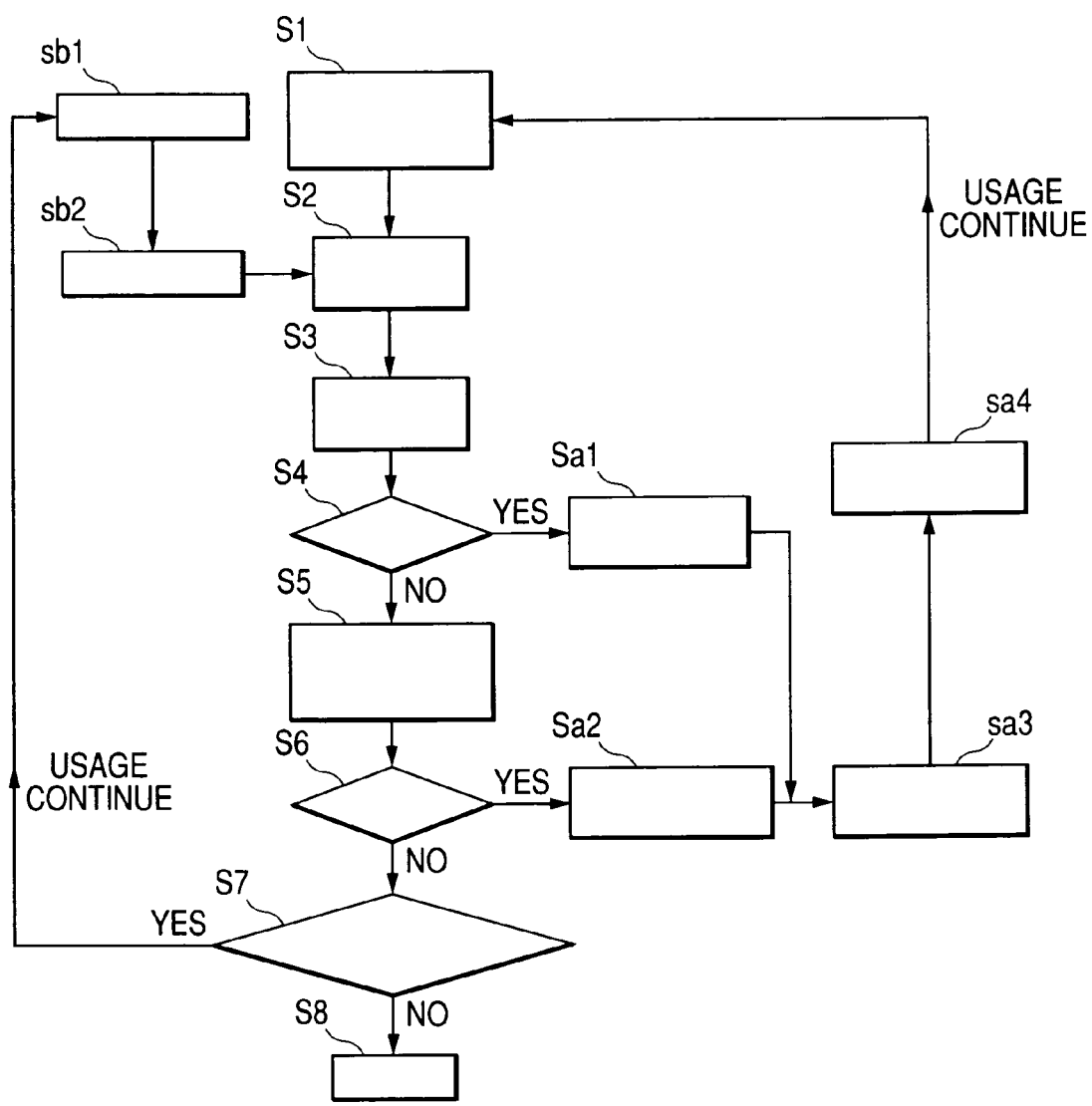
FIG. 9 is a flowchart illustrating a decision procedure in one embodiment of the invention.

One example of procedure for judging hydrogen embrittlement using the stress intensity factor $K_I$, critical stress intensity factor $K_{IH}$ for crack initiation, and critical stress intensity factor $K_{IC-H}$ for brittle fracture calculated as described above is next described by referring to FIG. 9

First, information about cracks in a material to be judged (pressure vessel), structural information, and information about the operation are entered (step S1). For example, as shown, the shape of cracked or damaged portion, initial flaw size, operating conditions, and so on are entered. Then, as already described based on the factors, the value of the stress intensity factor $K_I$ is calculated by a multivariable regression analysis (step S2). After calculating the value of $K_I$, the value of the critical stress intensity factor $K_{IH}$ for crack initiation is calculated on the condition of during shutdown at room temperature (step S3). After the calculation, the stress intensity factor $K_I$ and the critical stress intensity factor $K_{IH}$ for crack initiation are compared (step S4). Where the result of the comparison is that the relation, stress intensity factor $K_I$<critical stress intensity factor $K_{IH}$ for crack initiation, holds, it is estimated that the crack has not grown. The amount of growth $\Delta a$ is set to 0 (step Sa1). The program proceeds to step Sa2. On the other hand, where the result of the comparison in step S4 is that the relation, stress intensity factor $K_I \geq$ critical stress intensity factor $K_{IH}$ for crack initiation, holds, it is estimated that the crack has grown. The program goes to step S5 for calculating the critical stress intensity factor $K_{IC-H}$ for brittle fracture. In step S5, the factor $K_{IC-H}$ is calculated on the condition of during shutdown at room temperature, taking account of the degree of deterioration of the material as described previously. After the calculation, the stress intensity factor $K_I$ and the critical stress intensity factor $K_{IC-H}$ for brittle fracture are compared (step S6). Where the result of the comparison is that the relation, stress intensity factor $K_I$<critical stress intensity factor $K_{IC-H}$ for brittle fracture, holds, it is estimated that brittle fracture will not occur but the crack will have grown. The amount of growth $\Delta a$ is calculated (step Sa2). In this step Sa2, the growth rate of hydrogen embrittlement crack da/dt is calculated, using a mathematical formula and taking account of the rate of loading and the environmental temperature as described above. The amount of growth is predicted from the growth rate of crack. The program proceeds to the next step Sa3.

In step Sa3, the stress intensity factor $K_I$ is calculated on the condition of under pressurized operating conditions. In the next step Sa4, the heating temperature (T) is made appropriate using the stress intensity factor $K_I$ when under pressure. Specifically, with respect to the critical stress intensity factor $K_{IH}$ for crack initiation and critical stress intensity factor $K_{IC-H}$ for brittle fracture, the temperature dependence characteristics are expressed quantitatively as mentioned previously. The pressurizing temperature is set such that the relation in magnitude between the obtained $K_{IH}$, $K_{IC-H}$ values and the stress intensity factor $K_I$ is made appropriate. For example, if the stress intensity factor $K_I$ is lower than the critical stress intensity factor $K_{IC-H}$ for brittle fracture, it is estimated that the crack has not grown as described above. Since the crack is within the safe range in terms of evaluation of hydrogen embrittlement, the pressurizing temperature is set to satisfy the above-described conditions. If the present stress intensity factor $K_I$ is within the safe range, it is not necessary to change the pressurizing temperature. After the step of making appropriate the pressurizing temperature, the use of the equipment can be continued. If necessary, processing starting from step S1 is repeated.

On the other hand, where the result of the comparison in step S6 is that the relation, stress intensity factor $K_I \geq$ critical stress intensity factor $K_{IC-H}$ for brittle fracture, holds, it is judged that there is a possibility of brittle (rapid) fracture. The program goes to the next step S7, where the judged material is reevaluated in response to the result of the judgment. Where the result of the evaluation remains unchanged, a necessary repair or replacement is performed. On the other hand, where the result of the reevaluation of step S7 denies the possibility of rapid fracture, the use is continued. The operating conditions are reconsidered (step Sb1). Furthermore, the flaw size is measured (step Sb2). The program goes to step S2 and thus evaluation of hydrogen embrittlement is continued.

The hydrogen embrittlement of the judged material can be judged accurately and efficiently by performing the aforementioned procedure. Specific numerical values of the mathematical formulas used in the description made above are approximate values of experimental data collected using the following materials. They are not threshold values.

$K_{IC-H}$: effective at 20 to 86° C.
$K_{IH}$: effective at 20 to 150° C.
da/dt: effective where $\dot{K} > 0$ It is to be noted that this embodiment shows one form of the present invention and that the embodiment may be changed to a different embodiment within the scope of the present invention.

EXAMPLE

One example of the present invention is hereinafter described.

A high-temperature, high-pressure hydroprocessing reactor was used for about 26 years. A crack having a depth a=12.7 mm and a length 2c=50.8 mm occurred in a fillet weld of the internal attachment. It was detected that the crack extended through the base material. The specifications of the equipment are as follows. A method of judging and evaluating hydrogen embrittlement cracking using this equipment to which the present invention is applied is described below.

Figure 10:
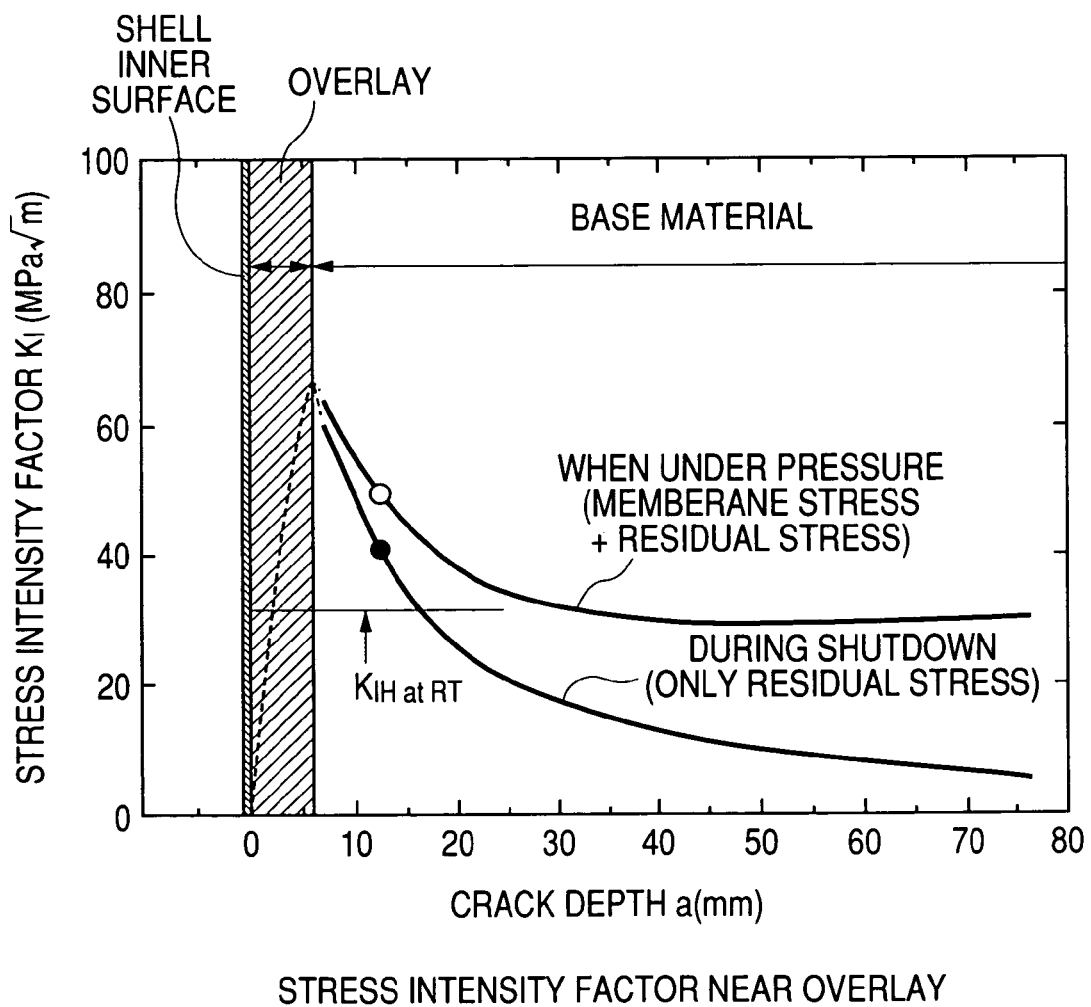
FIG. 10 shows the distributions of stress intensity factors during shutdown and under pressure, the distributions being calculated in one embodiment of the invention.

Specifications of the Equipment
  Design conditions:
  Pressure: 10.3 MPa
  Temperature: 454° C.
  Shutdown condition: 10° C./hr
  Inner diameter: 3048 mm
  Wall thickness: 152.4 mm (6.35 mm)
  Material: 2.25Cr-1Mo steel
  PWHT: executed (1) Calculation of Stress Intensity Factor The distribution of the stress intensity factors ($K_I$) at a cracked end portion generated by residual stress when the equipment is stopped at room temperature is found by an instantaneous simple calculational system. The distribution was found when the operation was stopped and when the operation was performed under pressure, and the results are shown in FIG. 10. As can be seen from this figure, when the operation was stopped, the relation $K_I$=41 MPa√m at the crack depth a=12.7 mm was reached.

(2) Judgment of Possibility of Growth of Crack

Using the mathematical formulas, $K_{IH}$ was found according to the degree of deterioration of the material, hydrogen, temperature, and loading environment reflected. The result is the critical stress intensity factor $K_{IH}$ for crack initiation when the equipment was stopped at a constant temperature was 31.4 MPa√m. Comparison with the stress intensity factor $K_I$ found in (1) above shows that $K_I > K_{IH}$. Therefore, it is judged that there is a possibility that the crack will grow at decreasing temperature during shutdown.

(3) Judgment of Fracture Toughness in Hydrogen Environment

The parameter $K_{IC-H}$ reflecting the degree of deterioration of material, hydrogen, temperature, and loading environment is found using the aforementioned mathematical formulas. The critical stress intensity factor for brittle fracture during shutdown at room temperature is $K_{IC-H}$=65.7 MPa$\sqrt{m}$. Comparison with the stress intensity factor $K_I$ found in (1) above reveals that $K_{IH}<K_I<K_{IC-H}$. In consequence, it is judged that the possibility of brittle fracture is low.

(4) Estimation of Amount of Growth of Crack Δa

The loading rate K when the reactor is stopped at 10° C./hr is calculated at 0.00013 MPa$\sqrt{m}$/s. It is assumed that the wall temperature is room temperature. The rate and temperature are substituted into the formula regarding the crack growth rate da/dt. The crack growth rate da/dt is roughly calculated at 0.5 mm/day. It is judged that the crack will continue to grow to the intersection with $K_{IH}$ in FIG. 10, i.e., will grow about 16 mm.

(5) Making Appropriate Temperature Under Pressure

Under pressure, the stress intensity factor $K_I$ is 49 MPa$\sqrt{m}$ as described above. The minimum pressurizing temperature that can be used to avoid cracking or fracture due to hydrogen embrittlement starting from a defect is calculated from the above formula at a minimum pressurizing temperature of 76° C. on the condition that the relation $K_I>K_{IH}$ is satisfied.

Figure 11:
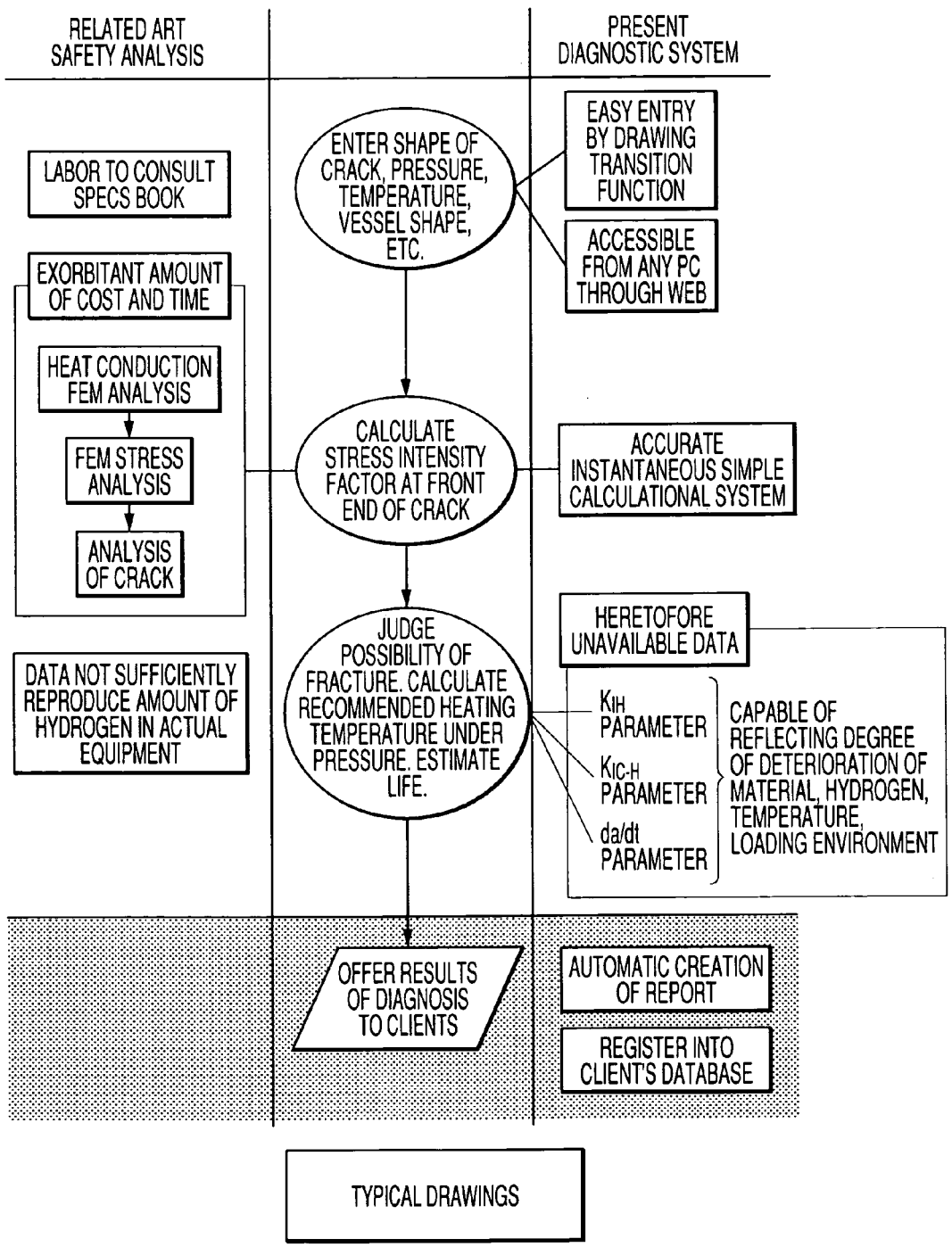
FIG. 11 is a flowchart illustrating a diagnostic system using a decision method of the present invention and a related art method of safety analysis.
Figure 12:
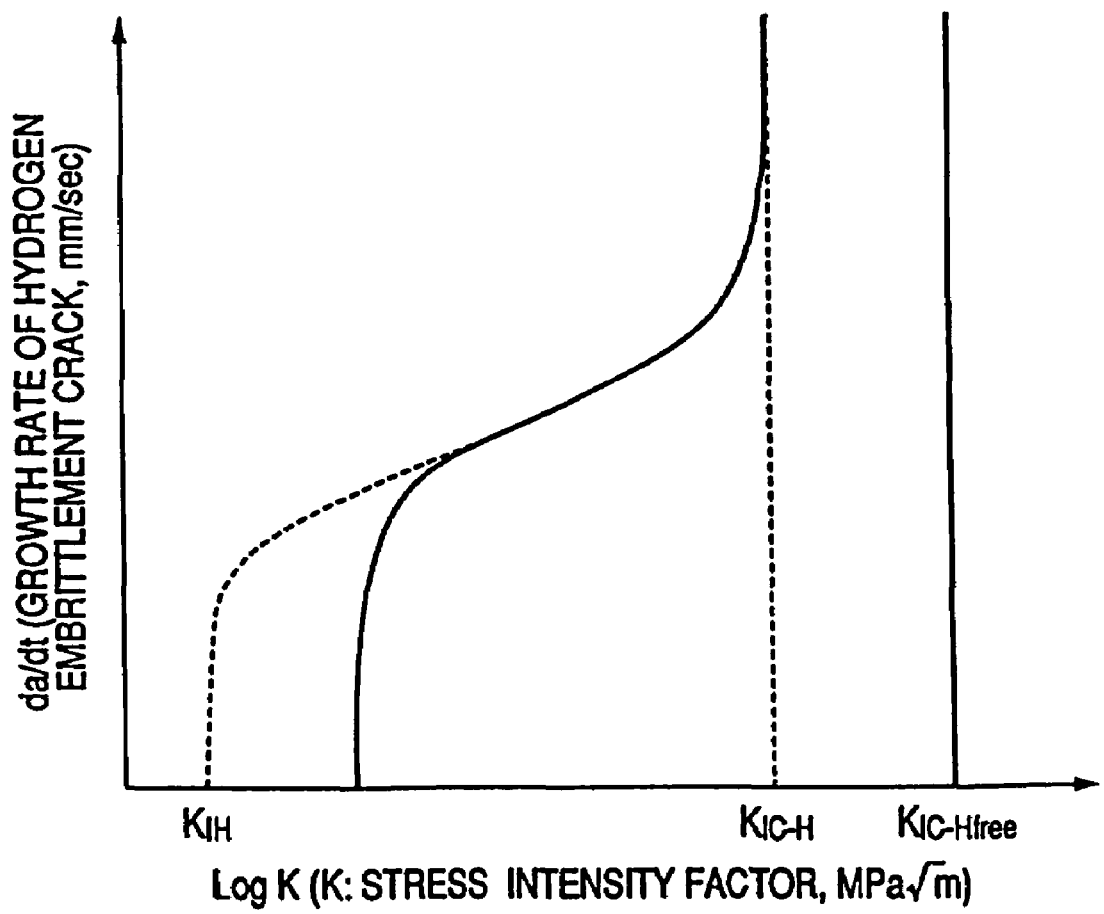
FIG. 12 is a schematic used for evaluation of hydrogen embrittlement crack growth as shown in API 1579.

A diagnostic system using a judgement method of the present invention and a related art method of safety analysis are shown and compared in the flowchart of FIG. 11.

In the diagnostic system of the invention, the shape of a crack, pressure, vessel size, and other factors can be easily entered through the WEB. The stress intensity factor at the crack tip can be quickly and accurately calculated by an instantaneous, simple calculational system that finds a regression formula by a multivariable regression analysis using the above-described input data as factors. The critical stress intensity factor $K_{IH}$ under presence of a crack, the critical stress intensity factor $K_{IC-H}$ for brittle fracture, and the hydrogen embrittlement crack growth rate da/dt reflecting the degree of deterioration of the material, hydrogen, temperature, and loading environment are calculated. Judgment of the possibility of fracture of the pressure vessel, calculation of the recommended pressurizing temperature, and estimation of the life can be performed accurately and efficiently, using these parameters and the stress intensity factor. The results of the judgments are offered as reports to individual users. Furthermore, data used for the judgments and the results of judgments can be registered in a client's database and utilized.

On the other hand, in the related art method, it is laborious to consult a specs book. Furthermore, sophisticated calculations are performed using a high-performance computer for FEM analysis. Consequently, a tremendous amount of cost and time is necessary. In addition, the obtained data does not permit sufficient reconstruction of the amount of hydrogen in actual equipment.

As described so far, the evaluation technique and system according to the present invention permit calculations to be performed efficiently and accurately to judge whether an embrittlement crack induced by high-temperature, high-pressure hydrogen gas filled in a pressure vessel for petroleum refining is permissible or not. Hence, novel safety diagnostic services can be offered.

What is claimed is:

1. A method of judging hydrogen embrittlement cracking of a material used in a high-temperature, high-pressure hydrogen environment, comprising the steps of:
    finding a stress intensity factor $K_I$ of a crack appeared in the material, based on factors including at least information about a position, a crack orientation, and a shape of the crack and information about a structure of the material; and
    judging a hydrogen embrittlement cracking of the material according to said stress intensity factor $K_I$,
    wherein said stress intensity factor $K_I$ is expressed by a regression formula obtained by performing a multivariable regression analysis using said factors.

2. A method of judging hydrogen embrittlement cracking of a material used in a high-temperature, high-pressure hydrogen environment as set forth in claim 1, wherein said material constitutes a pressure vessel, and said factors include a depth and a length of said crack, structural factors including a nozzle diameter, an inner diameter, a wall thickness, and an overlay thickness of the pressure vessel, and an operating pressure.

3. A method of judging hydrogen embrittlement cracking of a material used in a high-temperature, high-pressure hydrogen environment as set forth in claim 1,
    wherein said stress intensity factor $K_I$ and a critical stress intensity factor $K_{IH}$ for crack initiation are compared and a decision is made as to whether the crack has grown or not according to results of the comparison, and
    wherein said critical stress intensity factor $K_{IH}$ for crack initiation is a quantitative expression of temperature dependence characteristics that the material which has been temper embrittled shows in a range of from room temperature to 150° C. in a hydrogen absorbed state.

4. A method of judging hydrogen embrittlement cracking of a material used in a high-temperature, high-pressure hydrogen environment as set forth in claim 3, wherein the material includes a temper, embrittled steel which absorbs approximately 2.0 ppm hydrogen.

5. A method of judging hydrogen embrittlement cracking of a material used in a high-temperature, high-pressure hydrogen environment as set forth in claim 1,
    wherein said stress intensity factor $K_I$ and a critical stress intensity factor $K_{IC-H}$ for brittle fracture are compared and possibility of brittle fracture is judged according to results of the comparison, and
    wherein said critical stress intensity factor $K_{IC-H}$ for brittle fracture is a quantitative expression of temperature dependence characteristics that the material which has been temper embrittled shows in a range of from room temperature to 86° C. in a hydrogen absorbed state.

6. A method of judging hydrogen embrittlement cracking of a material used in a high-temperature, high-pressure hydrogen environment as set forth in claim 5, wherein the material includes a temper, embrittled steel which absorbs approximately 2.0 ppm hydrogen.

7. A method of judging hydrogen embrittlement cracking of a material used in a high-temperature, high-pressure hydrogen environment as set forth in claim 1, wherein a crack growth rate is judged according to a crack growth rate calculated from a rate of loading and from an operating temperature.

8. A method of judging hydrogen embrittlement cracking of a material used in a high-temperature, high-pressure hydrogen environment as set forth in claim 1, wherein said stress intensity factor $K_I$ is found on a shutdown condition.

9. A method of judging hydrogen embrittlement cracking of a material used in a high-temperature, high-pressure hydrogen environment as set forth in claim 1,
- wherein said stress intensity factor $K_I$ and a critical stress intensity factor $K_{IH}$ for crack initiation are compared and a decision is made as to whether the crack has grown or not according to results of the comparison,
- wherein said critical stress intensity factor $K_{IH}$ for crack initiation is a quantitative expression of temperature dependence characteristics that the material which has been temper embrittled shows in a range of from room temperature to 150° C. in a hydrogen absorbed state,
- wherein said stress intensity factor $K_I$ and a critical stress intensity factor $K_{IC\text{-}H}$ for brittle fracture are compared and possibility of brittle fracture is judged according to results of the comparison, and
- wherein said critical stress intensity factor $K_{IC\text{-}H}$ for brittle fracture is a quantitative expression of temperature dependence characteristics that the material which has been temper embrittled shows in a range of from room temperature to 86° C. in a hydrogen absorbed state.

10. A method of judging hydrogen embrittlement cracking of a material used in a high-temperature, high-pressure hydrogen environment as set forth in claim 9,
- wherein an operating temperature is set according to which of said stress intensity factor $K_I$ and said critical stress intensity factor $K_{IH}$ for crack initiation, the factor $K_{IH}$ being dependent on the temperature, or said critical stress intensity factor $K_{IC\text{-}H}$ for brittle fracture is greater, and
- wherein said material is a pressure vessel for petroleum refining.

11. A method of judging hydrogen embrittlement cracking of a material used in a high-temperature, high-pressure hydrogen environment as set forth in claim 9, wherein
- (A) said stress intensity factor $K_I$ found on a shutdown condition and said critical stress intensity factor $K_{IC\text{-}H}$ for brittle fracture are compared,
- (B) where when a decision is not made according to results of the comparison that there is a possibility of brittle fracture, stress intensity factor $K_I$ when under pressure is found on a condition that an operation is being performed under pressure, and
- (C) the operating temperature is set according to which of the stress intensity factor $K_I$ when under pressure and said critical stress intensity factor $K_{IH}$ for crack initiation, the factor $K_{IH}$ being dependent on temperature, or said critical stress intensity factor $K_{IC\text{-}H}$ for brittle fracture is greater, and
- wherein said material is a pressure vessel for petroleum refining.

* * * * *